US012569416B2

(12) United States Patent
Kitamura et al.

(10) Patent No.: US 12,569,416 B2
(45) Date of Patent: Mar. 10, 2026

(54) OIL-IN-WATER EMULSIFIED COSMETIC

(71) Applicant: L V M H RECHERCHE, Saint-Jean de Brave (FR)

(72) Inventors: Miyako Kitamura, Tokyo (JP); Mai Ozawa, Chiyoda-Ku (JP)

(73) Assignee: L V M H RECHERCHE, Saint-Jean de Braye (FR)

( * ) Notice: Subject to any disclaimer, the term of this patent is extended or adjusted under 35 U.S.C. 154(b) by 783 days.

(21) Appl. No.: 17/757,712

(22) PCT Filed: Dec. 20, 2019

(86) PCT No.: PCT/IB2019/001439

§ 371 (c)(1),
(2) Date: Jun. 17, 2022

(87) PCT Pub. No.: WO2021/123861

PCT Pub. Date: Jun. 24, 2021

(65) Prior Publication Data

US 2023/0031264 A1 Feb. 2, 2023

(51) Int. Cl.

| | |
|---|---|
| ***A61K 8/00*** | (2006.01) |
| ***A61K 8/06*** | (2006.01) |
| ***A61K 8/34*** | (2006.01) |
| ***A61K 8/55*** | (2006.01) |
| ***A61K 8/64*** | (2006.01) |
| ***A61K 8/73*** | (2006.01) |
| ***A61Q 1/00*** | (2006.01) |
| ***A61Q 1/14*** | (2006.01) |
| ***A61Q 17/04*** | (2006.01) |
| ***A61Q 19/00*** | (2006.01) |

(52) U.S. Cl.

CPC .............. *A61K 8/062* (2013.01); *A61K 8/345* (2013.01); *A61K 8/553* (2013.01); *A61K 8/64* (2013.01); *A61K 8/735* (2013.01); *A61Q 1/00* (2013.01); *A61Q 1/14* (2013.01); *A61Q 17/04* (2013.01); *A61Q 19/00* (2013.01)

(58) Field of Classification Search

CPC ........ A61K 8/062; A61K 8/345; A61K 8/553; A61K 8/64; A61K 8/735; A61K 8/73; A61Q 1/00; A61Q 1/14; A61Q 17/04; A61Q 19/00

See application file for complete search history.

(56) References Cited

FOREIGN PATENT DOCUMENTS

| | | | |
|---|---|---|---|
| CN | 107613952 | A | 1/2018 |
| EP | 3391872 | A1 | 10/2018 |
| JP | 2003277220 | A | 10/2003 |
| JP | 2008069075 | A | 3/2008 |
| JP | 2019214537 | A | * 12/2019 |
| KR | 20030064986 | A | 8/2003 |
| KR | 20180023537 | A | 3/2018 |

OTHER PUBLICATIONS

Fuchs Keratins and the Skin. Annu Rev Cell Dev Biol. 1995. 11, 123-53.*

Notice of Preliminary Rejection issued in counterpart Korean Patent Application No. 10-2022-7024183 on Feb. 17, 2025.

International Search Report and Written Opinion for Corresponding International Application No. PCT/IB2019/001439 mailing date Sep. 14, 2020.

* cited by examiner

*Primary Examiner* — Jeanette M Lieb

(74) *Attorney, Agent, or Firm* — Panitch Schwarze Belisario & Nadel LLP; Erin M. Dunston

(57) ABSTRACT

One aspect of the invention provides an oil-in-water emulsified cosmetic, which comprises in a cosmetically acceptable medium:

a) a hydrogenated lecithin,
b) an anionic surfactant derived from microorganisms,
c) a polyol comprising a glycerin,
d) a polysaccharide, wherein the content of the anionic surfactant preferably ranges from 0.005% to 1% by weight of the total weight of the oil-in-water emulsified cosmetic.

10 Claims, No Drawings

OIL-IN-WATER EMULSIFIED COSMETIC

CROSS REFERENCE TO RELATED APPLICATIONS

This application is a U.S. National Stage of International Patent Application No. PCT/IB2019/001439 filed Dec. 20, 2019, the disclosure of which is incorporated herein by reference in their entirety.

TECHNICAL FIELD

The present invention relates to an oil-in-water emulsified cosmetic.

BACKGROUND ART

Oil-in-water emulsified cosmetics having an oil component dispersed in an aqueous phase containing an aqueous component, are known as cosmetic formulations. Oil-in-water emulsified cosmetics are applied in skin care products because they can impart watery light sensation to skin due to their aqueous component and high moisturizing effect to skin due to their oil components.

With increasing orientation of consumers toward “natural” products in recent years, there is growing support for cosmetics that contain naturally-derived ingredients. KR20030064986A, for example, discloses a cosmetic in form of oil-in-water emulsion comprising lecithin or a lecithin derivative extracted from plants, and surfactin produced by *Bacillus subtilis*, as surfactants derived from natural substances. JP2008069075A also discloses skin care composition comprising sodium surfactin.

Technical Problem

It is often difficult to ensure the stability of quality for cosmetics that use naturally-derived ingredients. For example, when naturally derived surfactants are used, the emulsion stability tends to be inferior compared to using synthetic surfactants. Methods for increasing the emulsion stability of cosmetics using naturally-derived surfactants are therefore being investigated. For the cosmetic of KR 2003649861A, the emulsion stability is increased by reducing the average particle size of the emulsion particles to a range of 10 to 100 nm. Such emulsion is named ‘nano emulsion’. But cosmetics with small average particle sizes often cannot exhibit the texture desired for cosmetics, in particular when consumers search for feeling of richness during application (a feeling with a suitable degree of viscosity or thickness during application).

In addition, it is also required to exhibit the texture desired for cosmetics. For example, consumers search for feeling of low stickiness after application of cosmetics.

So it is an object of the present invention to provide an oil-in-water emulsified cosmetic having excellent emulsion stability and also low stickiness after application. Another object of the present invention is to provide an oil-in-water emulsified cosmetic having excellent emulsion stability, low stickiness after application, and even an excellent richness during application.

Solution to Problem

The present inventors have found that by selecting specific naturally-derived surfactants and combining them with specific components, it is possible to obtain an oil-in-water emulsified cosmetic that has high emulsion stability. It was also found that that the oil-in-water emulsified cosmetic has low stickiness when it is applied onto skin, and the present invention was thereupon completed. And the inventors even demonstrated that an oil-in-water emulsion of the invention is preferred for providing also a richness feeling during application, in comparison to nano emulsion.

SUMMARY OF THE INVENTION

According to one aspect of the invention there is provided an oil-in-water emulsified cosmetic comprising, in a cosmetically acceptable medium, a hydrogenated lecithin, an anionic surfactant derived from microorganisms, a polyol comprising a glycerin, and a polysaccharide. In a particular embodiment, content of the anionic surfactant ranges from 0.005 mass % to 1 mass % of the total weight of the oil-in-water emulsified cosmetic.

The “mass %” may also be referred to hereunder as “% by weight”.

The “oil-in-water emulsified cosmetic” may also be referred to hereunder as “oil-in-water emulsion” or “oil-in-water emulsion composition” or “cosmetic composition in form of an oil-in-water emulsion”.

The term “cosmetically or physiologically acceptable” means compatible with the keratinic materials, in particular the skin, which has a color, a smell and a pleasant touch and does not cause unacceptable discomfort (stinging, tautness).

With this cosmetic, creaming is less likely to form in the emulsion even after prolonged storage, while coalescence and separation of the emulsion are also less likely to occur, and therefore the emulsion stability is excellent. The oil-in-water emulsified cosmetic has high penetration into the skin and imparts a desirable feel including a watery sensation, smoothness and long-lasting moisture, while also having low stickiness after application. In addition, since the oil-in-water emulsified cosmetic uses naturally-derived surfactants, it is also an environmentally-friendly formulation.

In a particular embodiment, an average particle size of emulsion particles is 500 nm or larger. In this embodiment, the oil-in-water emulsified cosmetic of the invention is not a “nano emulsion”. The oil-in-water emulsified cosmetic in the embodiment has advantageously excellent richness when applied. That is, it is another object of the one aspect of the present invention to provide an oil-in-water emulsified cosmetic having excellent emulsion stability, low stickiness after application, and also excellent richness during application.

The term “richness during application” means a feeling with a suitable degree of viscosity or thickness during application.

The anionic surfactant is preferably sodium surfactin. A content of the polyol is preferably 5 mass % or greater of the total weight of the oil-in-water emulsified cosmetic. This can further increase the emulsion stability.

The oil-in-water emulsified cosmetic may also comprise an electrolyte. The electrolyte may include a cosmetic active.

The present invention also relates to a cosmetic process for caring for and/or making-up keratinic materials comprising the application onto keratinic materials, in particular onto skin, of the oil-in-water emulsified cosmetic as defined in the invention.

Advantageous Effects of Invention

According to the invention it is possible to provide an oil-in-water emulsified cosmetic having excellent emulsion stability and also low stickiness after application, in comparison to the previous cosmetics. And when the oil-in-water emulsified cosmetic is in form of a classical emulsion, ie not a nano emulsion, it even provides excellent richness during application.

DETAILED DESCRIPTION OF THE INVENTION

Embodiments of the invention will now be described. However, the present invention is not limited to the embodiments described below.

The cosmetic according to one embodiment is an oil-in-water emulsified cosmetic (a cosmetic consisting of an oil-in-water emulsion). In this cosmetic, an oil component is dispersed as particles in an aqueous phase that includes an aqueous component. In an oil-in-water emulsion, the oil component particles are also referred to as emulsion particles.

The oil-in-water emulsified cosmetic of this embodiment contains a hydrogenated lecithin, an anionic surfactant derived from microorganisms, a polyol comprising a glycerin, and a polysaccharide.

Hydrogenated Lecithin

The hydrogenated lecithin is lecithin that has been subjected to hydrogenation treatment, thus converting at least some of the unsaturated double bonds to saturated bonds. Hydrogenated lecithin includes hydrogenated lecithin from vegetable lecithin such as hydrogenated soybean lecithin, hydrogenated corn lecithin, hydrogenated palm lecithin and hydrogenated coconut lecithin. The hydrogenated lecithin is preferably hydrogenated soybean lecithin. A single type of hydrogenated lecithin may be used alone, or two or more different ones may be used in combination. If the oil-in-water emulsified cosmetic contains a hydrogenated lecithin, a stable lamellar structure is formed on the surfaces of the emulsion particles and the emulsion stability of the oil-in-water emulsified cosmetic can be increased. In addition, containing hydrogenated lecithin allows richness to be imparted during application while reducing stickiness after application.

From the viewpoint of further increasing emulsion stability, the hydrogenated lecithin content is preferably 0.1 mass % or greater, more preferably 0.2 mass % or greater and even more preferably 0.3 mass % or greater, and preferably no greater than 2 mass %, more preferably no greater than 1.5 mass % and even more preferably no greater than 1.0 mass %, based on the total weight of the oil-in-water emulsified cosmetic. In particular, the hydrogenated lecithin content is comprises between 0.1% to 2%, preferably from 0.2% to 1.5%, more preferably from 0.3% to 1%, by weight of the total weight of the emulsified cosmetic of the invention.

Anionic Surfactants Derived from Microorganisms

Examples of anionic surfactants derived from microorganisms include lipopeptides or their salts such as surfactins, arthrofactins and sodium surfactin, and fatty acids such as spiculisporic acid. The anionic surfactant derived from microorganisms preferably includes a lipopeptide or its salt, and more preferably includes a surfactin or its salt, from the viewpoint of promoting formation of emulsion particles to further increase the emulsion stability. A single one of these anionic surfactants derived from microorganisms may be used, or two or more different ones may be used in combination.

A surfactin is a cyclic lipopeptide represented by the following formula (1).

(1)

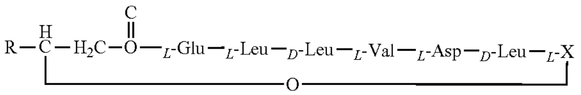

In the formula, X represents an amino acid residue selected from the group consisting of leucine, isoleucine, valine, glycine, serine, alanine, threonine, asparagine, glutamine, aspartic acid, glutamic acid, lysine, arginine, cysteine, methionine, phenylalanine, tyrosine, tryptophan, histidine, proline, 4-hydroxyproline and homoserine, and R represents a straight-chain or branched alkyl group of 8 to 14 carbon atoms. X is preferably leucine.

Surfactin salts include sodium salt, potassium salt, monoethanolamine salt, diethanolamine salt, triethanolamine salt, lysine salt and arginine salt. The surfactin salt is preferably sodium salt (sodium surfactin).

When sodium surfactin is to be used as the anionic surfactant derived from microorganisms, a commercial product may be used. An example of a commercial product of sodium surfactin that may be used is KANEKA Surfactin (product of Kaneka Corp.).

In a particular embodiment, the content of the anionic surfactant derived from microorganisms is no greater than 1 mass % of the total weight of the oil-in-water emulsified cosmetic. This can increase emulsion stability and reduce stickiness of the oil-in-water emulsified cosmetic. From the same viewpoint, the content of the anionic surfactant derived from microorganisms is preferably no greater than 0.8 mass %, no greater than 0.6 mass %, no greater than 0.5 mass %, no greater than 0.3 mass %, no greater than 0.1 mass %, no greater than 0.08 mass % or no greater than 0.06 mass %, based on the total weight of the oil-in-water emulsified cosmetic. From the viewpoint of increasing the emulsion stability, the content of the anionic surfactant derived from microorganisms is preferably 0.005 mass % or greater, more preferably 0.01 mass % or greater and even more preferably 0.02 mass % or greater, based on the total weight of the oil-in-water emulsified cosmetic.

From this viewpoint, the content of the anionic surfactant derived from microorganisms may be 0.005 to 1 mass %, 0.01 to 1 mass %, 0.02 to 1 mass %, 0.005 to 0.8 mass %, 0.01 to 0.8 mass %, 0.02 to 0.8 mass %, 0.005 to 0.6 mass %, 0.01 to 0.6 mass %, 0.02 to 0.6 mass %, 0.005 to 0.5 mass %, 0.01 to 0.5 mass %, 0.02 to 0.5 mass %, 0.005 to 0.3 mass %, 0.01 to 0.3 mass %, 0.02 to 0.3 mass %, 0.005 to 0.1 mass %, 0.01 to 0.1 mass %, 0.02 to 0.1 mass %, 0.005 to 0.08 mass %, 0.01 to 0.08 mass %, 0.02 to 0.08 mass %, 0.005 to 0.06 mass %, 0.01 to 0.06 mass % or 0.02 to 0.06 mass %, based on the total weight of the oil-in-water emulsified cosmetic.

In particular, the content of the anionic surfactant derived from microorganisms is between 0.005% to 1%, in particular from 0.01% to 0.8%, preferably from 0.02% to 0.6%, and even preferably from 0.02% to 0.1% by weight of total weight of the oil-in-water emulsified cosmetic of the invention.

Polysaccharide

The oil-in-water emulsified cosmetic contains a polysaccharide. This can increase the emulsion stability and the level of richness during application. Polysaccharides include xanthan gum, guar gum, locust bean gum, *Tremella fuciformis*-produced polysaccharides, carrageenan, agars and sodium hyaluronate. The polysaccharide is preferably a naturally-derived polysaccharide, and more preferably a polysaccharide derived from a microorganism, such as a xanthan gum and a sodium hyaluronate. These polysaccharides may be used alone or in combinations of two or more different types. The oil-in-water emulsified cosmetic may also contain two or more different types of polysaccharides.

In a particular embodiment, the oil-in-water emulsified cosmetic comprises a polysaccharide selected from xanthan gum sodium hyaluronate, and mixtures thereof.

From the viewpoint of further increasing the richness during application, the polysaccharide(s) content is preferably 0.005 mass % or greater, more preferably 0.01 mass % or greater and even more preferably 0.05 mass % or greater, and no greater than 3 mass %, no greater than 2 mass %, no greater than 1 mass %, no greater than 0.5 mass %, no greater than 0.3 mass % or no greater than 0.2 mass %, based on the total weight of the oil-in-water emulsified cosmetic.

In a particular embodiment, the total content of polysaccharide(s) is ranges from 0.005% to 3%, in particular from 0.05% to 2%, preferably from 0.1 to 1% by weight of total weight of the oil-in-water emulsified cosmetic.

Polyol

The oil-in-water emulsified cosmetic contains at least one polyol (polyhydric alcohol) comprising at least glycerin. A polyol is a compound with two or more hydroxyl groups (—OH), and it is preferably an aliphatic compound. A polyol comprising a glycerin may be glycerin alone, or it may be a combination of glycerin with another polyol. If the oil-in-water emulsified cosmetic contains a polyol comprising a glycerin, the level of richness during application can be increased. In addition, the hydrogenated lecithin and anionic surfactant derived from microorganisms will satisfactory dissolve, allowing the emulsion stability to be increased. If the polyol include a glycerin, the emulsion stability is further increased.

The number of hydroxyl groups in a polyol other than glycerin may be 2 or more or 3 or more, and it may be up to 10, up to 8, up to 6 or up to 4. The number of carbon atoms of the polyol may be, for example, one or more, 2 or more or 3 or more, and up to 10, up to 8 or up to 6.

Examples of polyols other than glycerin include glycols such as butylene glycols (such as 1,3-butylene glycol), pentylene glycols (such as 1,2-pentanediol), propanediols (such as 1,3-propanediol and propylene glycol), dipropylene glycol and hexanediols (such as 1,2-hexanediol); glycerols such as diglycerin and polyglycerin; and sugar alcohols such as sorbitol, glycerol, xylitol, mannitol and erythritol. These polyols other than glycerin may be used alone or in combinations of two or more.

In a particular embodiment, the oil-in-water emulsified cosmetic of the invention comprises at least glycerin and another polyol selected from butylene glycol, propanediol, and mixtures thereof.

The total content of the polyol(s) comprising glycerin is preferably 5 mass % or greater based on the total weight of the oil-in-water emulsified cosmetic. This can further increase the emulsion stability. The total content of the polyol(s) comprising glycerin is more preferably 6 mass % or greater and even more preferably 8 mass % or greater, and no greater than 30 mass %, no greater than 25 mass %, no greater than 20 mass %, no greater than 15 mass % or no greater than 12 mass %, based on the total weight of the oil-in-water emulsified cosmetic. In a particular embodiment, the total content of polyols comprising glycerin, and preferably glycerin, butylene glycol and propanediol, ranges from 5 to 30 mass %, in particular from 6 to 25 mass %, preferably from 8 to 15 mass %, based on the total weight of the oil-in-water emulsified cosmetic. From the same viewpoint, the content of the polyol comprising a glycerin may be 5 to 30 mass %, in particular 6 to 30 mass %, 6 to 25 mass %, 6 to 20 mass %, 6 to 15 mass %, 6 to 12 mass %, 8 to 30 mass %, 8 to 25 mass %, 8 to 20 mass %, 8 to 15 mass % or 8 to 12 mass %, based on the total weight of the oil-in-water emulsified cosmetic.

The content of glycerin in the total content of the polyol(s) is preferably 20 mass % or greater, more preferably 30 mass % or greater and even more preferably 40 mass % or greater based on the total weight of the polyol, from the viewpoint of further increasing the emulsion stability. The content of glycerin may be 100 mass %, or up to 80 mass % or up to 60 mass %, based on the total weight of the polyol(s).

Oily Phase

In the oil-in-water emulsified cosmetic of this embodiment, the oil component is present as emulsion particles. According to one embodiment, the oil component includes an oil agent.

Oil agents may be vegetable fats and oils, wax, hydrocarbon oil, higher fatty acids, higher alcohols, ester oils, silicone oils or the like, which are oil agents commonly used in cosmetics. The oil agent may be in liquid form, in paste form or in solid form.

Examples of vegetable fats or oils include meadowfoam oil, olive fruit oil, *camellia* oil, coconut oil, macadamia nut oil, rose hip oil, avocado oil, sunflower seed oil, rice bran oil, castor oil, almond oil, mango seed butter, *Paeonia suffruticosa* seed oil, murumuru seed butter and shea butter.

Examples of waxes include vegetable waxes such as jojoba seed oil, carnauba wax and candelilla wax.

Examples of hydrocarbon oils include liquid paraffin, paraffin, vaseline, ceresin, dodecane, isododecane, tetradecane, isotetradecane, hexadecane, isohexadecane, squalane, polybutene, polyisobutene, hydrogenated polyisobutene and olefin oligomers.

Examples of higher fatty acids include lauric acid, myristic acid, palmitic acid, stearic acid and isostearic acid.

Examples of higher alcohols include cetyl alcohol, isostearyl alcohol, 2-octyldodecanol and behenyl alcohol.

Examples of ester oils include isopropyl myristate, 2-octyldodecyl myristate, cetyl 2-ethylhexanoate, isononyl isononanate, dicaprylyl carbonate, polyglyceryl diisostearate, diglyceryl triisostearate, glyceryl tribehenate and diisostearyl malate.

Examples of silicone oils include polydimethylsiloxane (dimethicone), polymethylphenylsiloxane (diphenyldimethicone), phenyltrimethicone and diphenylsiloxyphenyltrimethicone.

Of the oil agents mentioned above, naturally-derived oil agents are preferred for use. Naturally-derived oil agents may be vegetable fats or oils such as meadowfoam oil; waxes such as jojoba seed oil; or squalane and the like.

The oil agent(s) total content may be 1 mass % or greater, 2 mass % or greater or 3 mass % or greater, and no greater than 30 mass %, no greater than 20 mass % or no greater than 10 mass %, based on the total weight of the oil-in-water emulsified cosmetic.

In a particular embodiment, the total content of oil agent (s) ranges from 1% to 30%, in particular from 2% to 20% by weight of the total weight of the composition.

Additional Ingredients

The oil-in-water emulsified cosmetic may also contain an electrolyte. As used herein, an electrolyte is a component different from the aforementioned hydrogenated lecithin, surfactant derived from a microorganism, polysaccharide, polyol and oil agent, which ionizes in the oil-in-water emulsified cosmetic to function as an active ingredient, pH regulator, preservative, or the like.

The electrolyte may be one that is commonly used in cosmetics, such as an organic electrolyte or inorganic electrolyte, for example. Examples of organic electrolytes include malic acid, citric acid, lactic acid, tartaric acid, glycolic acid, edetic acid, succinic acid, ascorbic acid and their salts. In this embodiment, the organic electrolyte includes examples of active ingredient, for examples vitamin derivatives such as ascorbic acid 2-glucoside and sodium tocopheryl phosphate; amino acids such as trimethylglycine and adenosine, and derivatives of the same. Examples of inorganic electrolytes include sodium hydroxide, sodium chloride, magnesium chloride, calcium chloride, aluminum potassium sulfate and sodium hydrogenphosphate. A single electrolyte may be used alone, or two or more may be used in combination.

In a particular embodiment, the oil-in-water emulsified cosmetic does not contain, as an ascorbic acid salt, L-ascorbic acid-2-phosphoric acid ester magnesium sodium salt, represented by the following formula (A).

(A)

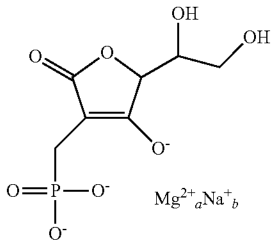

[In the formula, a and b represent equivalents, a being 0.3 to 1.1, b being 0.8 to 2.4, and the value of 2a+b being 2.7 to 3.3.]

The content of the electrolyte may be 0.05 mass % or greater, 0.1 mass % or greater or 0.15 mass % or greater, and no greater than 10 mass %, no greater than 9 mass %, no greater than 8 mass %, no greater than 5 mass %, no greater than 3 mass %, no greater than 1 mass % or no greater than 0.5 mass %, based on the total weight of the oil-in-water emulsified cosmetic. In a particular embodiment, the total content of electroyte may range from 0.05% to 10%, in particular from 0.1% to 5% by weight of total weight of the oil-in-water emulsified cosmetic of the composition.

The oil-in-water emulsified cosmetic may further contain surfactants other than an anionic surfactant derived from microorganisms, such as anionic surfactants, cationic surfactants and nonionic surfactants. Other surfactants that are commonly employed in cosmetics may be used as appropriate. The oil-in-water emulsified cosmetic does not need to contain a glycerin mono fatty acid ester as a surfactant.

The oil-in-water emulsified cosmetic may further contain a polymer other than a polysaccharide. Other polymers that are commonly employed in cosmetics may be used as appropriate.

The oil-in-water emulsified cosmetic may also contain a monohydric alcohol such as ethanol. A monohydric alcohol functions as a preservative, for example, in the oil-in-water emulsified cosmetic. The oil-in-water emulsified cosmetic does not need to contain phenoxyethanol or phenoxyisopropanol as a monohydric alcohol.

In addition to the components mentioned above, the oil-in-water emulsified cosmetic may also contain, as appropriate, additives that are commonly used in cosmetics, including preservatives such as chlorphenesin and hydroxyacetophenone, antioxidants, pigments or perfumes. The oil-in-water emulsified cosmetic may also contain a powder such as an inorganic powder and organic powder, in order to adjust texture of the oil-in-water emulsified cosmetic. The powder that is commonly employed in cosmetics may be used as appropriate.

In a particular and preferred embodiment, is not in form of a nano emulsion. In nano emulsion, the oil is generally in the form of droplets having a number average particle size of 250 nm or less, preferably 10 nm to 200 nm. In the particular and preferred embodiment of the invention, the average particle size of the emulsion particles forming the oil-in-water emulsion is 500 nm or larger. This can provide excellent richness when the oil-in-water emulsified cosmetic has been applied to skin. The average particle size may be 600 nm or larger, or 700 nm or larger, and it may be no larger than 100 μm, no larger than 50 μm, no larger than 10 μm, or no larger than 5 μm.

By "average particle size" is meant by the median size D [50] by volume representing the maximum size that 50% by volume the particles.

The sizes are measured by static light scattering by means of a commercial particle size analyzer (for example, a DelsaMax CORE by Beckman Coulter), making it possible to apprehend the particle size distribution of all the particles over a wide range ranging from 0.01 μm to 1000 pm. The data are processed on the basis of the classical Mie scattering theory. This theory is the most suitable for size distributions ranging from submicron to multi-micron, it allows to determine an "effective" diameter of particles. This theory is particularly described in Van de Hulst, HC, "Light Scattering by Small Particles", Chapters 9 and 10, Wiley, New York, 1957. D [50] represents the maximum size that presents 50% by volume the particles. The average particle size of the emulsion particles can be adjusted by adjusting of stirring condition when emulsifying the cosmetic.

The oil-in-water emulsified cosmetic of this embodiment can be produced by heating a hydrogenated lecithin, an anionic surfactant derived from microorganisms, a glycerin-including polyol, an oil component and water (at 60 to 100° C., for example), and then uniformly mixing them, and subsequently adding other materials and stirring to mix them.

The method for obtaining the oil-in-water emulsified cosmetic of this embodiment ('non nano emulsion') does not require substantial mechanical energy for production, for example does not require a high-pressure emulsification treatment, as it is requested for obtaining nano emulsion. In a particular embodiment, the oil-in-water emulsified cosmetic of the invention is obtained by mixing and stirring the phases between 1000 rpm to 5000 rpm, in particular 1000 rpm to 3000 rpm, to uniformity. The method for obtaining the oil-in-water emulsified cosmetic in form of a nano emulsion, that may be another embodiment of the invention, with excellent stability and non stickyness but with low richness feeling during application, comprises the use of substantial mechanical energy, especially a high-pressure emulsification treatment, for example high-pressure emulsification treatment 3 times at 200 MPa, using a high-pressure emulsifier (Starburst mini, product of Sugino Machine, Ltd.) as illustrated further in the example 2.

The 25° C. viscosity of the oil-in-water emulsified cosmetic of this embodiment may be 1 to 100000 mPa·s. The 25° C. viscosity of the oil-in-water emulsified cosmetic is preferably 10 mPa·s or higher, 50 mPa·s or higher or 100 mPa·s or higher, and preferably no higher than 50000 mPa·s, no higher than 10000 mPa·s or no higher than 1000 mPa·s. The viscosity can be measured by measuring the shear viscosity using a rotating viscometer (for example, a Rheolab QC by Anton Paar GmbH, at a rotational speed of 100 rpm).

The oil-in-water emulsified cosmetic described above can be used as a skin care cosmetic or makeup cosmetic, such as lotion, milk, essence, makeup remover, makeup base, sunscreen, foundation or concealer, for example.

The present invention also relates to a cosmetic process for caring for and/or making-up keratinic materials comprising the application onto keratinic materials, in particular onto skin, of the oil-in-water emulsified cosmetic as defined in the invention.

The application of said oil-in-water emulsified cosmetic provide low stickiness after application. In a particular embodiment, when the oil-in-water emulsified cosmetic is in form of a non nano emulsion, the said composition even provide excellent richness during application, that is specifically advantageous for dry skin and mixed skin.

Examples

The invention will now be illustrated by examples, with the understanding that the invention is not meant to be limited to these examples.

<Preparation of Oil-In-Water Emulsified Cosmetic>

For Example 1 and Comparative Examples 1 to 4, oil-in-water emulsified cosmetics were obtained by the following method based on the compositions listed in Table 1. The ingredients listed in the compositions are expressed in mass weight % by total mass weight of the composition.

Comparative example 1: no anionic surfactant derived from microorganisms
Comparative example 2: no hydrogenated lecithin
Comparative example 3: no polyols
Comparative example 4: no glycerin For Example 1, first, the hydrogenated soybean lecithin (Emulmetik™ 950, product of Lucas Meyer Cosmetics Canada, Inc.), sodium surfactin (KANEKA Surfactin, product of Kaneka Corp.), polyols (A) and oil agents (B) were each heated to 80° C., and then (B) was added to (A) and a stirrer was used for stirring at 3000 rpm, mixing them to uniformity. Water (C) heated to 80° C. was then added to the mixture, and mixing was continued under the same conditions. Next, polysaccharides (D) was added to the mixture and stirring was carried out at 80° C. for 3000 rpm, after which the mixture was cooled to room temperature. Finally, preservatives, ethanol and a perfume (E) and electrolytes (F) were added, and a stirrer was used for stirring at 1000 rpm, mixing them to uniformity.

For Example 2, an oil-in-water emulsified cosmetic in form of nano emulsion was obtained by the following method comprising an high-pressure emulsification treatment, based on the composition listed in Table 1. First, the hydrogenated lecithin, sodium surfactin, polyols (A) and oil agents (B) were each heated to 80° C., and then (B) was added to (A) and a stirrer was used for stirring at 3000 rpm, mixing them to uniformity. Half of the water (C) heated to 80° C. was then added to the mixture, and mixing was continued under the same conditions. Next, the mixture was subjected to high-pressure emulsification treatment 3 times at 200 MPa, using a high-pressure emulsifier (Starburst mini, product of Sugino Machine, Ltd.). Separately, polysaccharides (D) was added to the remaining half of the water (C) and a stirrer was used for mixing to uniformity at 80° C., 3000 rpm, after which the mixture was cooled to room temperature to prepare a polysaccharide solution. After adding preservatives, ethanol and a perfume (E), and electrolytes (F) to the polysaccharide solution, a stirrer was used for mixing to uniformity at 1000 rpm, after which the previous high-pressure emulsified mixture was added to it.

<Measurement of Average Particle Size>

In each prepared oil-in-water emulsified cosmetic, the average particle size of the emulsion particles was measured by the dynamic light scattering method using a particle size measuring device (DelsaMax CORE: product of Beckman Coulter). The average particle size (D[50]) of each cosmetic is shown in Table 1.

<Emulsion Stability Evaluation>

Each oil-in-water emulsified cosmetic of the Examples and Comparative Examples was filled into a transparent glass container and sealed. It was then placed in a thermostatic bath at 50° C. and allowed to stand for 1 month. After standing, the emulsion stability was visually evaluated based on the following evaluation scale. An evaluation of 'B' corresponds to excellent emulsion stability, and an evaluation of 'A' corresponds to particularly excellent emulsion stability.

A: Particularly excellent emulsion stability
B: Excellent emulsion stability
C: Some emulsion stability
D: No emulsion stability, e.g coalescence or separation <Organoleptic Evaluation>

The oil-in-water emulsified cosmetics of the Examples and Comparative Examples were organoleptically evaluated for non-stickiness after application and richness during application. For the organoleptic evaluation, each cosmetic was coated onto skin by a cosmetic expert evaluation panel, and the evaluation was conducted based on the following evaluation scale. An evaluation of 'B' corresponds to non-stickiness or excellent richness, and an evaluation of 'A' corresponds to particularly non-stickiness or excellent richness.

(1) Non-stickiness after application
A: Absolutely no stickiness
B: Almost no stickiness
C: Some stickiness
D: Stickiness (2) Richness during application
A: Particularly excellent richness
B: Excellent richness
C: Some richness
D: Absolutely no richness The results presented in the Table 1 show that the combination of an hydrogenated lecithin, an anionic surfactant derived from microorganisms, and a polyol comprising at least glycerin, and a polysaccharide, provide an oil-in-water emulsified cosmetic having excellent emulsion stability and low stickiness after application, in comparison with other comparative examples. And the evaluation of richness during application demonstrate that and oil-in-water emulsified cosmetic of the invention not in form of a nano emulsion (example 1) even has excellent richness during application when compared to the same composition but in form of nano emulsion (example 2). So depending of the searched performances (stability, non-stickyness and optionally richness during application) and the type of skin to be applied on (dry skin, mixed skin or greasy skin), man would prefer either the embodiment of nano emulsion composition, either the preferred embodiment of non nano emulsion composition.

TABLE 1

| | | | Examples | | Comp. Examples | | | |
|---|---|---|---|---|---|---|---|---|
| | | | 1 | 2 | 1 | 2 | 3 | 4 |
| A | Hydrogenated lecithin | | 0.5 | 0.5 | 0.5 | — | 0.5 | 0.5 |
| | Anionic surfactant derived from microorganisms | Sodium surfactin | 0.05 | 0.05 | — | 0.5 | 0.05 | 0.05 |
| | Polyol | Glycerin | 5 | 5 | 5 | 5 | — | — |
| | | 1,3-Butylene glycol | 4 | 4 | 4 | 4 | — | 4 |
| | | Propanediol | 1 | 1 | 1 | 1 | — | 1 |
| B | Oil | Meadowfoam seed oil | 2.5 | 2.5 | 2.5 | 2.5 | 2.5 | 2.5 |
| | | Squalane | 2.5 | 2.5 | 2.5 | 2.5 | 2.5 | 2.5 |
| C | Water | | qsp 100 | qsp 100 | qsp 100 | qsp 100 | qsp 100 | qsp 100 |
| D | Polysaccharide | Xanthan gum | 0.1 | 0.1 | 0.1 | 0.1 | 0.1 | 0.1 |
| | | *Alcaligenes* polysaccharides | 0.05 | 0.05 | 0.05 | 0.05 | 0.05 | 0.05 |
| | | Sodium hyaluronate | 0.01 | 0.01 | 0.01 | 0.01 | 0.01 | 0.01 |
| E | Preservative | Chlorphenesin | 0.2 | 0.2 | 0.2 | 0.2 | 0.2 | 0.2 |
| | | Hydroxyacetophenone | 0.2 | 0.2 | 0.2 | 0.2 | 0.2 | 0.2 |
| | Ethanol | | 5 | 5 | 5 | 5 | 5 | 5 |
| | Perfume | | 0.1 | 0.1 | 0.1 | 0.1 | 0.1 | 0.1 |
| F | Electrolytes | Ascorbic acid 2-glucoside | 0.1 | 0.1 | 0.1 | 0.1 | 0.1 | 0.1 |
| | | Trimethylglycine | 0.1 | 0.1 | 0.1 | 0.1 | 0.1 | 0.1 |
| | | Adenosine | 0.05 | 0.05 | 0.05 | 0.05 | 0.05 | 0.05 |
| | | Sodium tocopheryl phosphate | 0.01 | 0.01 | 0.01 | 0.01 | 0.01 | 0.01 |
| | | Sodium hydroxide | 0.01 | 0.01 | 0.01 | 0.01 | 0.01 | 0.01 |
| Average particle size of emulsion particles (nm) | | | 700 | 100 | 2000 | 800 | 2000 | 1500 |
| Emulsion stability | | | A | A | C | D | D | C |
| Organoleptic evaluation | | Non-stickiness after application | A | B | C | C | B | C |
| | | Richness during application | A | D | A | D | C | B |

The invention claimed is:

1. An oil-in-water emulsified cosmetic comprising, in a cosmetically acceptable medium:

a) a hydrogenated lecithin, b) sodium surfactin, c) at least one polyol comprising glycerin, and d) a polysaccharide, wherein the content of sodium surfactin ranges from 0.005% to 1% by weight of the total weight of the oil-in-water emulsified cosmetic.

2. The oil-in-water emulsified cosmetic according to claim 1, wherein the average particle size of emulsion particles is of at least 500 nm.

3. The oil-in-water emulsified cosmetic according to claim 1, wherein the polysaccharide is selected from xanthan gum, sodium hyaluronate and mixtures thereof.

4. The oil-in-water emulsified cosmetic according to claim 1, wherein it comprises glycerin, and at least another polyol selected from butylene glycol, propanediol and mixtures thereof.

5. The oil-in-water emulsified cosmetic according to claim 1, wherein the total content of the polyol(s) ranges from 5% to 30% by weight of the total weight of the oil-in-water emulsified cosmetic.

6. The oil-in-water emulsified cosmetic according to claim 1, which further comprises an electrolyte.

7. The oil-in-water emulsified cosmetic according to claim 1, in form of a skin care cosmetic or makeup cosmetic.

8. The oil-in-water emulsified cosmetic according to claim 7, in form of lotion, milk, essence, makeup remover, makeup base, sunscreen, foundation or concealer.

9. A cosmetic process for caring for and/or making-up keratinic materials, comprising the application onto keratinic materials, of the oil-in-water emulsified cosmetic as defined in claim 1.

10. The cosmetic process of claim 9, wherein the oil-in-water emulsified cosmetic is applied onto skin.

* * * * *